US012685535B2

(12) United States Patent
Knodel et al.

(10) Patent No.: US 12,685,535 B2
(45) Date of Patent: Jul. 21, 2026

(54) APPLICATOR FOR WOUND CLOSURE DEVICE

(71) Applicant: ZSX Medical, LLC, Moorestown, NJ (US)

(72) Inventors: Bryan Knodel, Flagstaff, AZ (US); Vincent Biondo, Flemington, NJ (US); Kaylah Ruiz, Moorestown, NJ (US); John Crombie, East Hanover, NJ (US); Anthony Bellezza, Moorestown, NJ (US); Dan Mazzucco, Haddon Heights, NJ (US)

(73) Assignee: ZSX MEDICAL, LLC, Moorestown, NJ (US)

(*) Notice: Subject to any disclaimer, the term of this patent is extended or adjusted under 35 U.S.C. 154(b) by 91 days.

(21) Appl. No.: 18/645,138

(22) Filed: Apr. 24, 2024

(65) Prior Publication Data
US 2024/0358372 A1     Oct. 31, 2024

Related U.S. Application Data

(60) Provisional application No. 63/461,751, filed on Apr. 25, 2023.

(51) Int. Cl.
*A61B 17/10*     (2006.01)
*A61B 17/08*     (2006.01)
*A61B 17/00*     (2006.01)

(52) U.S. Cl.
CPC ............ *A61B 17/10* (2013.01); *A61B 17/083* (2013.01); *A61B 2017/00367* (2013.01)

(58) Field of Classification Search
CPC .... A61B 2017/2932; A61B 2017/2933; A61B 2017/2934; A61B 2017/2936; A61B 2017/2925; A61B 2017/2913; A61B 2017/2916; A61B 2017/2915; A61B 17/28; A61B 17/083; A61B 17/10
See application file for complete search history.

(56) References Cited

U.S. PATENT DOCUMENTS

| | | | |
|---|---|---|---|
| 5,100,420 A | 3/1992 | Green et al. |
| 5,358,506 A | 10/1994 | Green et al. |
| 5,433,721 A | 7/1995 | Hooven et al. |
| 5,609,599 A | 3/1997 | Levin |
| 5,681,330 A | 10/1997 | Hughett et al. |

(Continued)

*Primary Examiner* — Majid Jamialahmadi
(74) *Attorney, Agent, or Firm* — Panitch Schwarze Belisario & Nadel LLP

(57) ABSTRACT

An applicator for a wound closure device includes a proximal handle and a barrel extending from the handle. The barrel includes an elongate shaft, a slidable elongate actuator, and an elongate, slidable ejector rod. A jaw is pivotably attached to a distal end of the elongate actuator. The jaw has a first pair of prongs and the shaft distally terminates in a second pair of prongs. The first and second pairs of prongs are configured to releasably receive the wound closure device. A single trigger is attached to the handle and is actuatable to a first position configured to enable loading of the wound closure device to the first and second pairs of prongs, a second position configured to open the loaded wound closure device, a third position configured to close the loaded wound closure device, and a fourth position configured to release the wound closure device from the applicator.

19 Claims, 9 Drawing Sheets

(56)            References Cited

U.S. PATENT DOCUMENTS

|  |  |  |
|---|---|---|
| 6,716,232 B1 | 4/2004 | Vidal et al. |
| 9,358,008 B2 | 6/2016 | Mazzucco et al. |
| 9,700,324 B2 | 7/2017 | Mazzucco et al. |
| 11,147,557 B1 | 10/2021 | Butch et al. |
| 2002/0068946 A1 | 6/2002 | Kortenbach et al. |
| 2003/0023249 A1 | 1/2003 | Manetakis |
| 2007/0093856 A1 | 4/2007 | Whitfield et al. |
| 2007/0213747 A1 | 9/2007 | Monassevitch et al. |
| 2008/0234705 A1 | 9/2008 | Cropper et al. |
| 2010/0089970 A1 | 4/2010 | Smith et al. |
| 2012/0022584 A1 | 1/2012 | Donnigan et al. |
| 2021/0212689 A1* | 7/2021 | Castro ................ A61B 17/1285 |

* cited by examiner

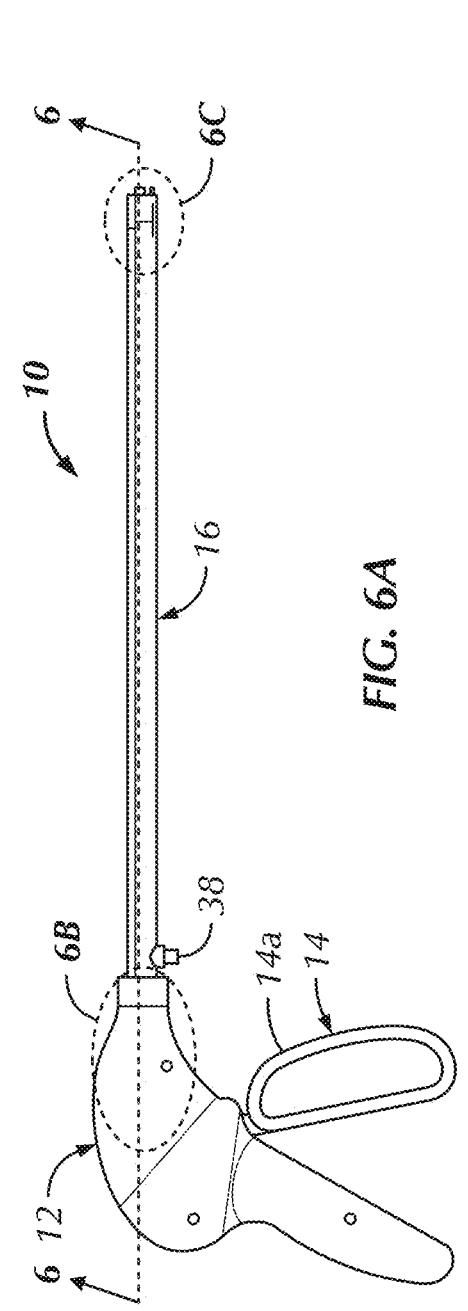
FIG. 6A
FIG. 6B
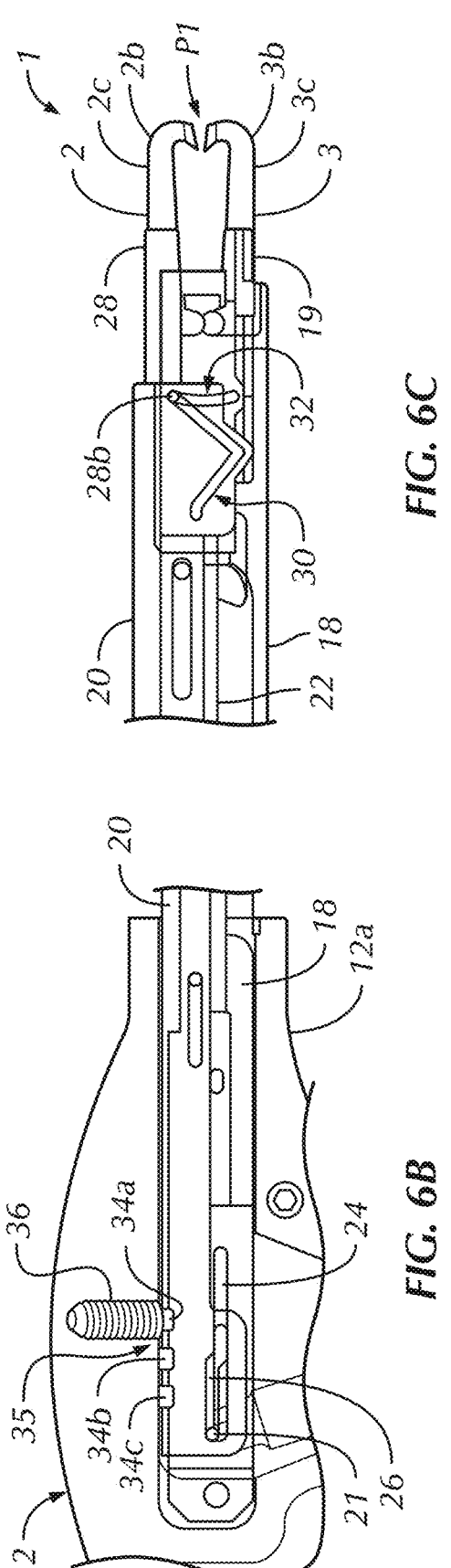
FIG. 6C

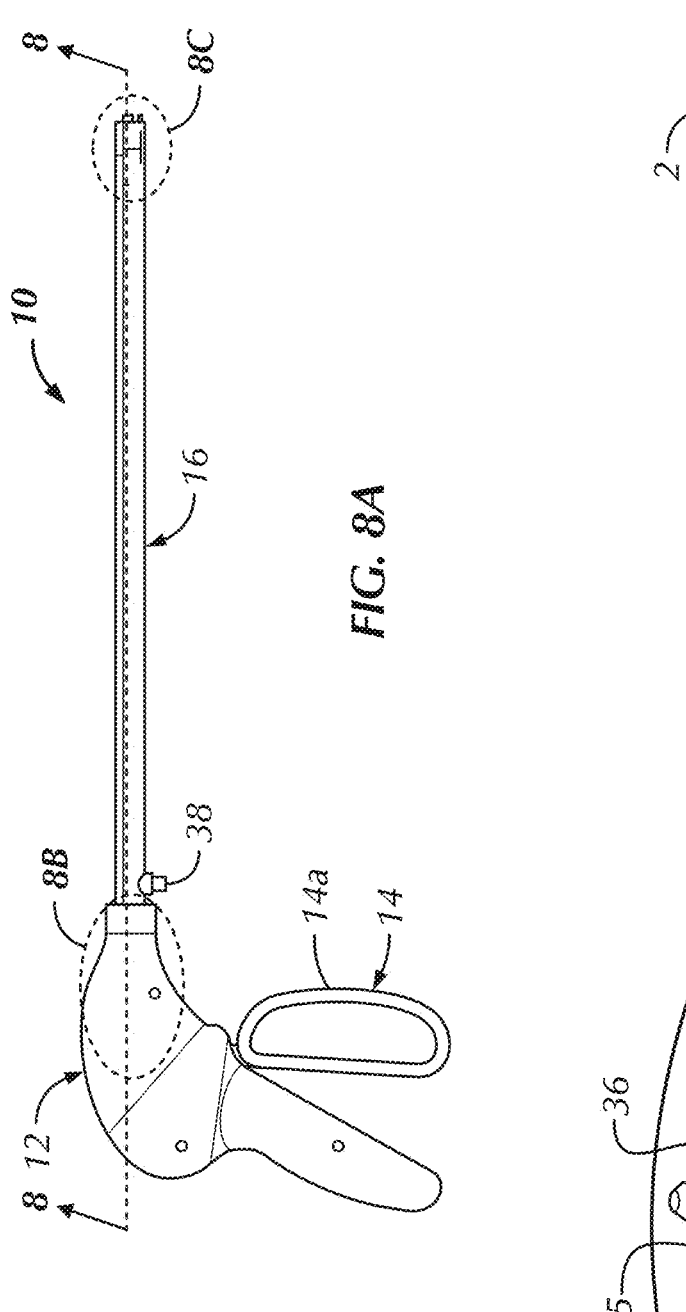
FIG. 8A
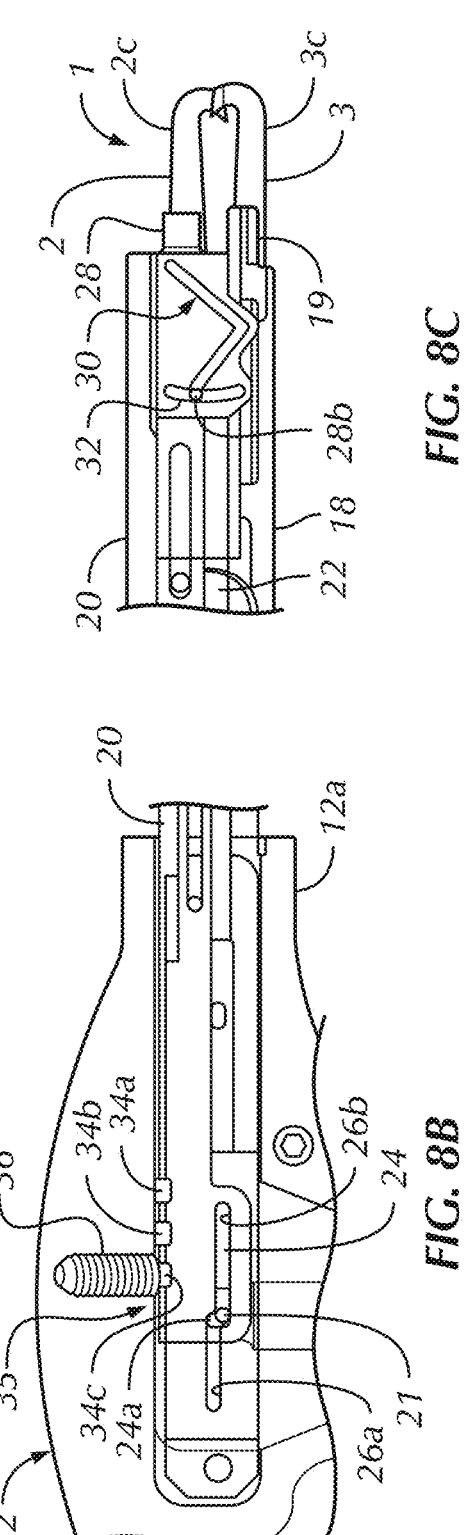
FIG. 8C
FIG. 8B

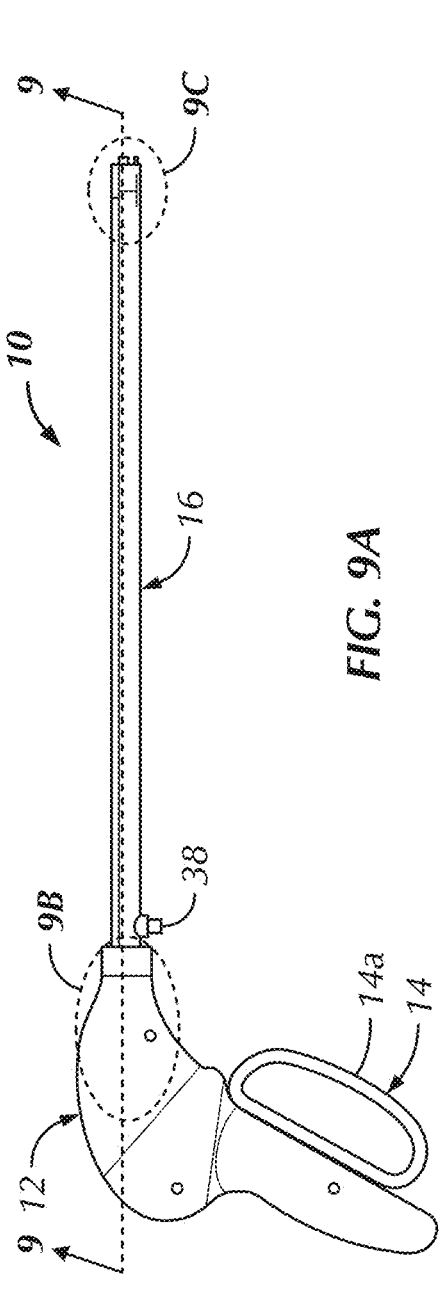
FIG. 9A
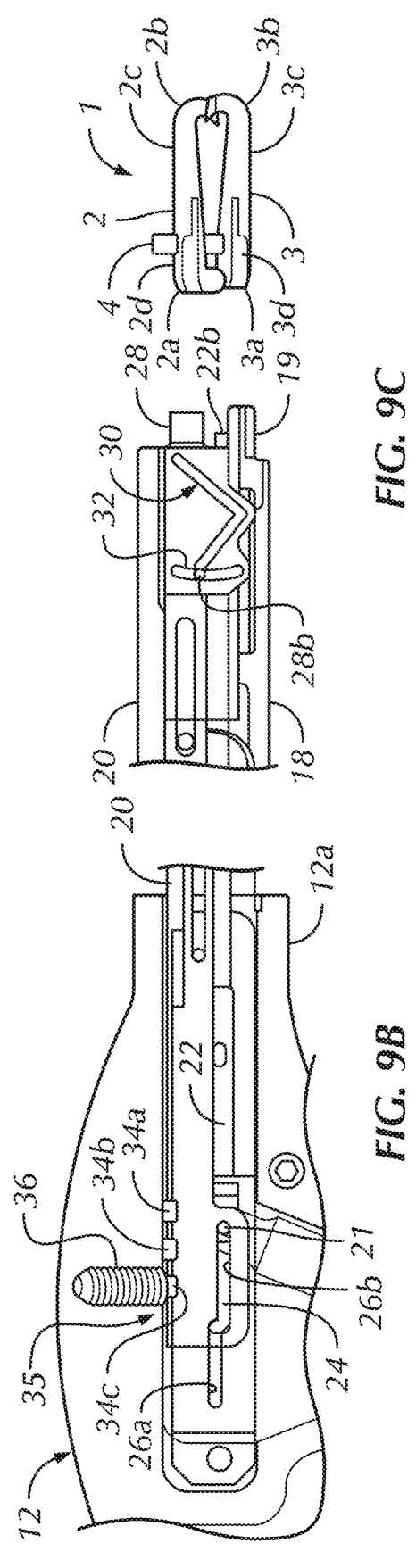
FIG. 9C
FIG. 9B

APPLICATOR FOR WOUND CLOSURE DEVICE

CROSS-REFERENCE TO RELATED APPLICATION

This application claims priority from similarly-titled U.S. Provisional Patent Application No. 63/461,751, filed Apr. 25, 2023, the entire contents of which are incorporated by reference herein.

BACKGROUND OF THE DISCLOSURE

The disclosure relates to a medical device applicator and, more particularly, to an incision or wound closure device applicator.

Closure devices are traditionally employed by medical personnel for effective and efficient closing of an incision or wound. Use of such closure devices is beneficial to mitigate the risk of post-operative surgical site infections (SSI).

It would, therefore, be advantageous to manufacture an applicator for such closure devices to enable simple and efficient application of the closure device(s) to the incision or wound site.

BRIEF SUMMARY OF THE DISCLOSURE

Briefly stated, one aspect of the present disclosure is directed to an applicator for a wound closure device. The applicator includes a proximal handle and a barrel extending from the handle. The barrel includes an elongate shaft, a slidable elongate actuator, and an elongate, slidable ejector rod. A jaw is pivotally attached to a distal end of the elongate actuator. The jaw has a first pair of prongs and the shaft distally terminates in a second pair of prongs. The first and second pairs of prongs are configured to releasably receive the wound closure device. A single trigger is attached to the handle and is actuatable to a first position configured to enable loading of the wound closure device to the first and second pairs of prongs, a second position configured to open the loaded wound closure device, a third position configured to close the loaded wound closure device, and a fourth position configured to release the wound closure device from the applicator.

In one configuration, the shaft is secured to the handle in a stationary manner and each of the elongate actuator and the ejector rod are slidably engaged with the handle.

In any one of the previous configurations, the elongate actuator includes an actuator slot and the shaft includes a shaft slot. In one configuration, an upper end of the trigger defines a fork and a proximal end of the ejector rod defines a clevis, the fork being pivotally attached to the clevis via a pin, the pin also extending transversely through the actuator slot and through the shaft slot. In one configuration, the shaft slot includes a first, proximal axial portion and a second, distal axial portion, joined together by a third and intermediate, transition portion, the first axial portion being spaced in relation to the second axial portion. In one configuration, the actuator slot is axially oriented and generally linear, a proximal end of the actuator slot including a protuberance extending upwardly therefrom, wherein the protuberance is aligned with the proximal portion of the shaft slot and a remainder of the actuator slot is aligned with the distal portion of shaft slot.

In any one of the previous configurations, the applicator further includes a detent mechanism, the detent mechanism comprising three successive depressions formed in an upper end of the elongate actuator and a spring-loaded member positioned to engage one of the three depressions.

In any one of the previous configurations, in the first position of the single trigger: (i) the spring-loaded member is positioned in a first depression of the three depressions; and (ii) the pin is positioned within the protuberance of the actuator slot and within the proximal axial portion of the shaft slot.

In any one of the previous configurations, in the second position of the single trigger: the spring-loaded member is positioned in a second depression of the three depressions; (ii) the pin is distally advanced within the proximal axial portion of the shaft slot relative to the position thereof in the first position of the single trigger; (iii) the pin remains within the protuberance of the actuator slot, thereby distally advancing the elongate actuator relative to the position thereof in the first position of the single trigger; and (iv) the ejector rod is distally advanced relative to the position thereof in the first position of the single trigger.

In any one of the previous configurations, in the third position of the single trigger: (i) the spring-loaded member is positioned in a third depression of the three depressions; (ii) the pin is distally advanced into the intermediate, transition portion of the shaft slot, coinciding with a proximal end of the distal axial portion of the shaft slot; (iii) the pin exits the protuberance of the actuator slot; and (iv) the ejector rod is distally advanced relative to the position thereof in the second position of the single trigger.

In any one of the previous configurations, in the fourth position of the single trigger: (i) the spring-loaded member is positioned in a third depression of the three depressions; (ii) the pin is distally advanced within the distal axial portion of the shaft slot relative to the position thereof in the third position of the single trigger; (iii) the shaft and the elongate actuator remain in the same respective positions thereof as in the third position of the single trigger; and (iv) the ejector rod is distally advanced relative to the position thereof in the third position of the single trigger and configured to contact and eject the wound closure device from the applicator.

In any one of the previous configurations, successive proximal gripping of the single trigger transitions the single trigger from the first position to the fourth position, and retraction of the single trigger transitions the single trigger from the fourth position to the first position.

In any one of the previous configurations, each of the first and second pairs of prongs include a respective pair of axially directed and laterally inwardly extending ribs.

In any one of the previous configurations, the second pair of prongs are fixedly secured to the shaft in a stationary manner.

In any one of the previous configurations, the jaw further includes a pin projecting laterally outwardly from the jaw and extending through a camming slot formed in a sidewall of the elongate actuator and extending through a generally vertical, support slot formed in a sidewall of the shaft. In one configuration, each generally vertical, support slot is generally arcuate. In any one of the previous configurations the camming slot defines three continuous legs, a first leg of the three continuous legs angularly declining from an upper distal end thereof to a lower proximal end thereof, a second leg of the three continuous legs angularly inclining from a lower distal end thereof to an upper proximal end thereof, and the third leg of the three continuous legs extending generally axially and proximally from the upper proximal end of the second leg. In one configuration, the pin is positioned proximate the upper distal end of the first leg of the camming slot and proximate an upper end of the support slot, and the first pair of prongs is oriented substantially parallel with the second pair of prongs, in the first position of the single trigger. In one configuration, the pin is positioned proximate the lower proximal end of the first leg of the camming slot and proximate a lower end of the support slot, and the first pair of prongs are angled away from the second pair of prongs, in the second position of the single trigger. In one configuration, the pin is positioned in the third leg of the camming slot, and the first pair of prongs is oriented substantially parallel with the second pair of prongs, in the third position of the single trigger.

BRIEF DESCRIPTION OF THE SEVERAL VIEWS OF THE DRAWINGS

The following description of embodiments of the disclosure will be better understood when read in conjunction with the appended drawings. It should be understood, however, that the disclosure is not limited to the precise arrangements and instrumentalities shown. In the drawings:

FIG. 6A is a side elevational view of the applicator of FIG. 1 in a loading position;

FIG. 6B is an enlarged, partial cross-sectional view of the handle of the applicator of FIG. 6A, taken along sectional line 6-6 of FIG. 6A;

FIG. 6C is an enlarged, partial cross-sectional view of a distal end of the applicator of FIG. 6A, taken along sectional line 6-6 of FIG. 6A;

FIG. 8A is a side elevational view of the applicator of FIG. 1 in a closing position;

FIG. 8B is an enlarged, partial cross-sectional view of the handle of the applicator of FIG. 8A, taken along sectional line 8-8 of FIG. 8A;

FIG. 8C is an enlarged, partial cross-sectional view of a distal end of the applicator of FIG. 8A, taken along sectional line 8-8 of FIG. 8A;

FIG. 9A is a side elevational view of the applicator of FIG. 1 in an ejecting position;

FIG. 9B is an enlarged, partial cross-sectional view of the handle of the applicator of FIG. 9A, taken along sectional line 9-9 of FIG. 9A; and FIG. 9C is an enlarged, partial cross-sectional view of a distal end of the applicator of FIG. 9A, taken along sectional line 9-9 of FIG. 9A.

DETAILED DESCRIPTION OF THE DISCLOSURE

Figure 1:
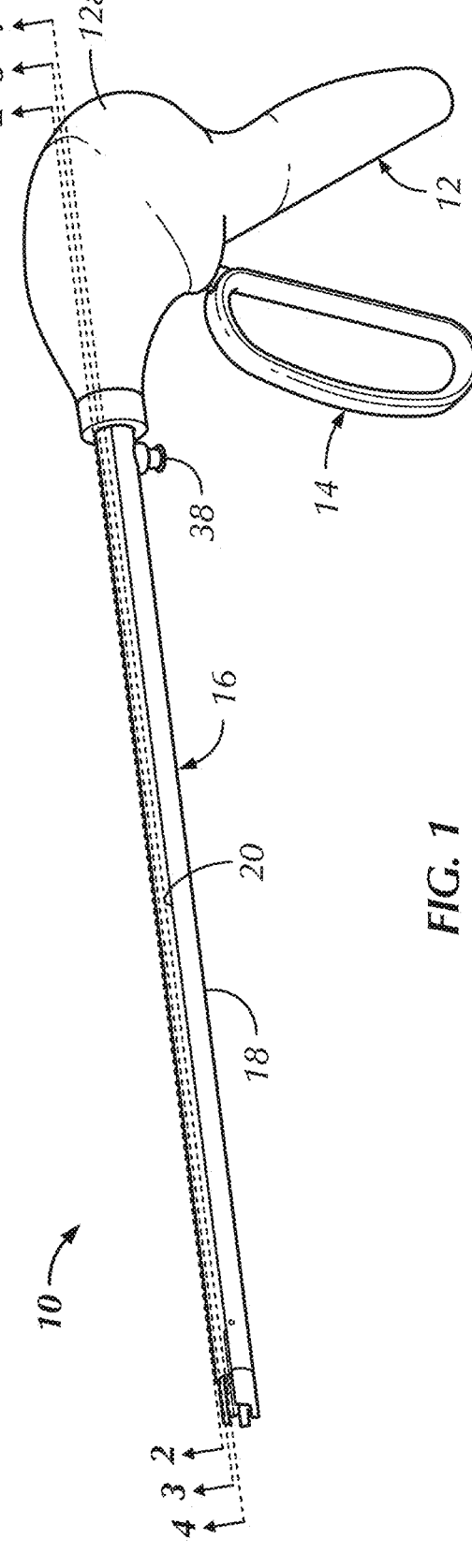
FIG. 1 is a top and side perspective view of an applicator in accordance with an embodiment of the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the applicator, and designated parts thereof, in accordance with the present disclosure. In describing the applicator, the terms proximal and distal are used in relation to the user, proximal being closer to the user and distal being further from the user. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-9C, an applicator, generally designated 10, for an incision or wound closure device 1 in accordance with an embodiment of the present disclosure. The closure device, such as, for example, as disclosed in U.S. Pat. No. 9,358,008, which is incorporated herein by reference in its entirety, may operate as an incision or wound closure device and may be utilized surgically. Generally, the closure device 1 includes a first clamping arm 2, a second clamping arm 3, and a flexible pin 4 maintained between the first and second clamping arms 2, 3 in a press-fit relationship. Each of the first and second clamping arms 2, 3 has a proximal first end 2a, 3a, an opposing distal second end 2b, 3b and a sidewall 2c, 3c extending therebetween (FIGS. 6C, 7C, 8C, 9C). As shown best in FIG. 9C, the sidewalls 2c, 3c each define a respective elongate and laterally inwardly directed recess 2d, 3d therein, axially extending from the respective proximal first side 2a, 3a along a portion of the axial extent of the sidewalls 2c, 3c. The closure device 1 has a first position P1 (FIG. 6C) in which the proximal first ends 2a, 3a of the first and second clamping arms 2, 3 partially engage or do not engage each other and a second position P2 in which the proximal first ends 2a, 3a of the first and second clamping arms 2, 3 pivotally engage each other (FIG. 7C). In the second position P2 of the closure device 1, a compressive force F generated at the proximal first ends 2a, 3a is transferred through the first and second clamping arms 2, 3 to the distal second ends 2b, 3b, as further described below.

Figure 2:
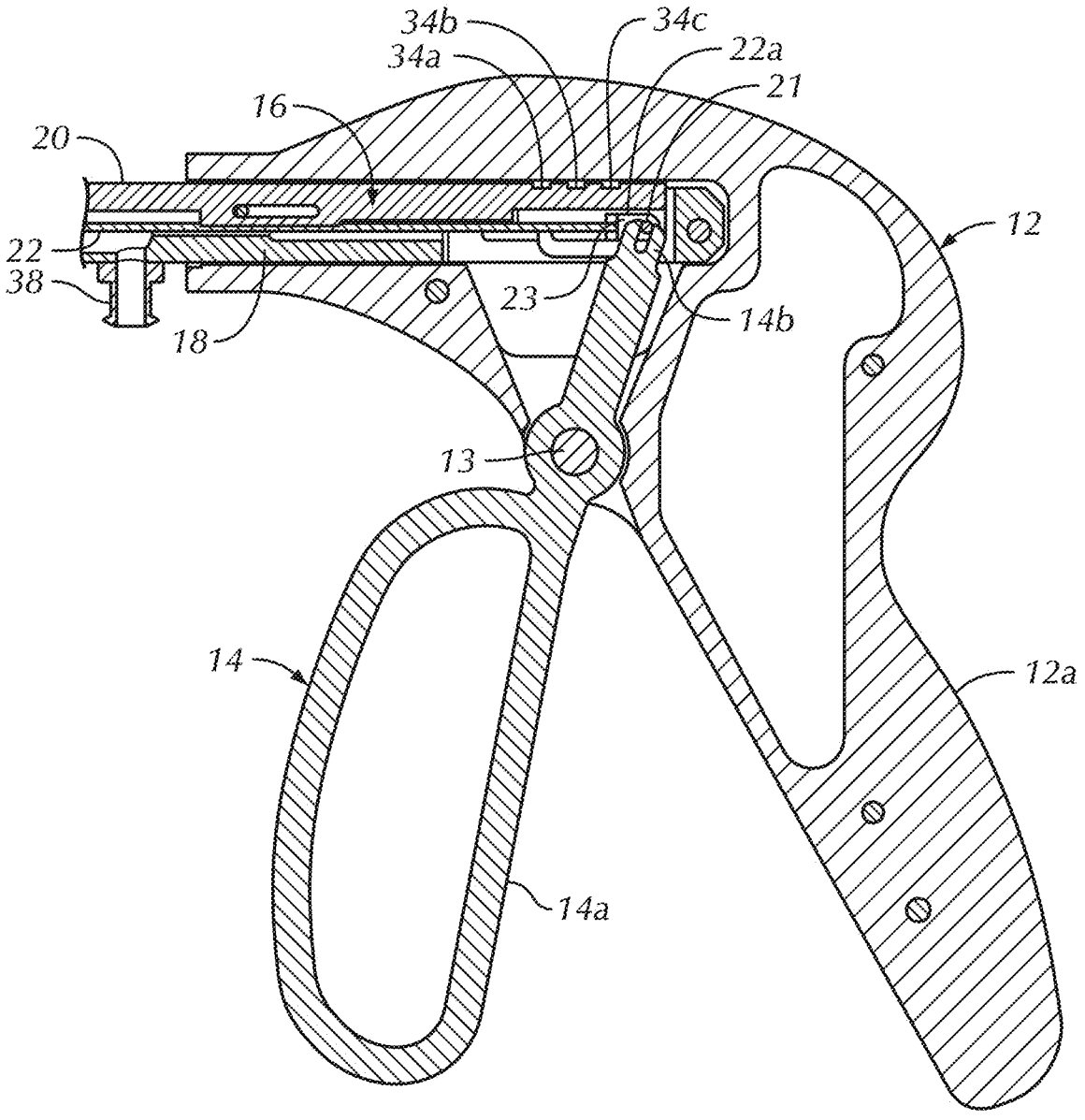
FIG. 2 is an enlarged, partial cross-sectional view of the applicator of FIG. 1, showing a handle and a single trigger thereof along sectional line 2-2 of FIG. 1.
Figure 3:
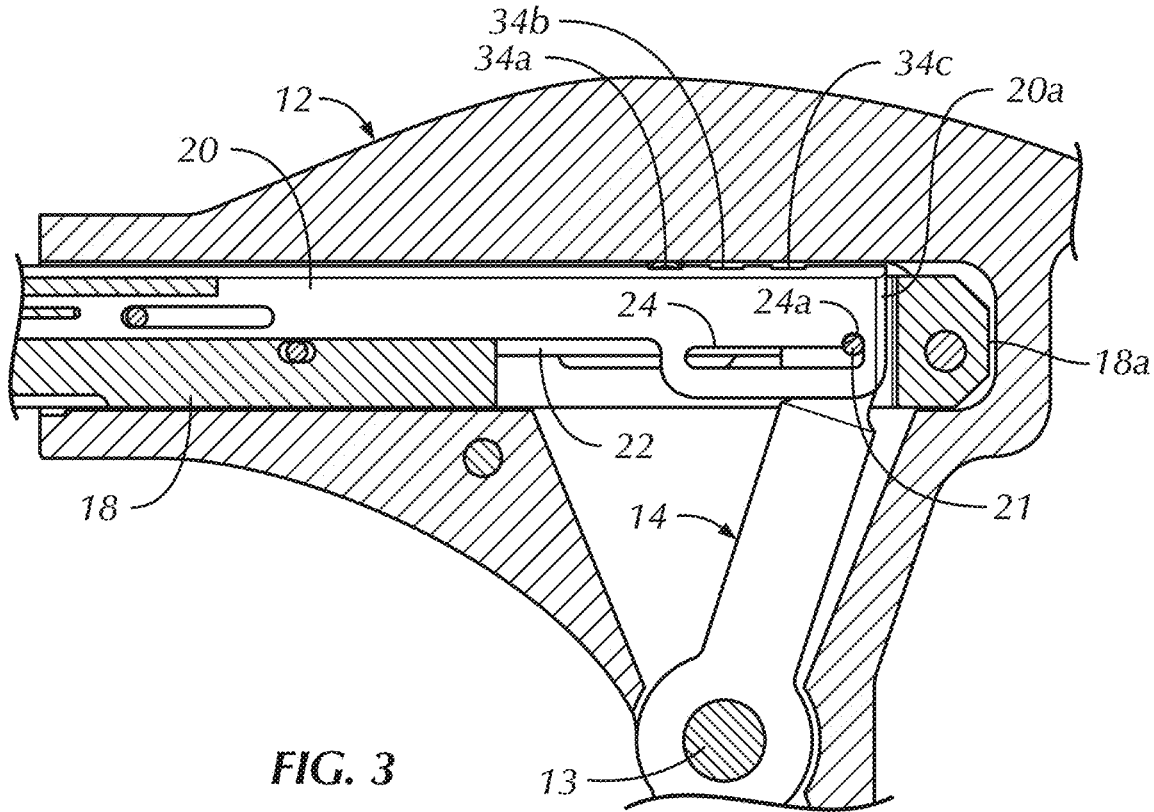
FIG. 3 is an enlarged, partial cross-sectional view of the handle and single trigger of the applicator of FIG. 1, along sectional line 3-3 of FIG. 1.
Figure 4:
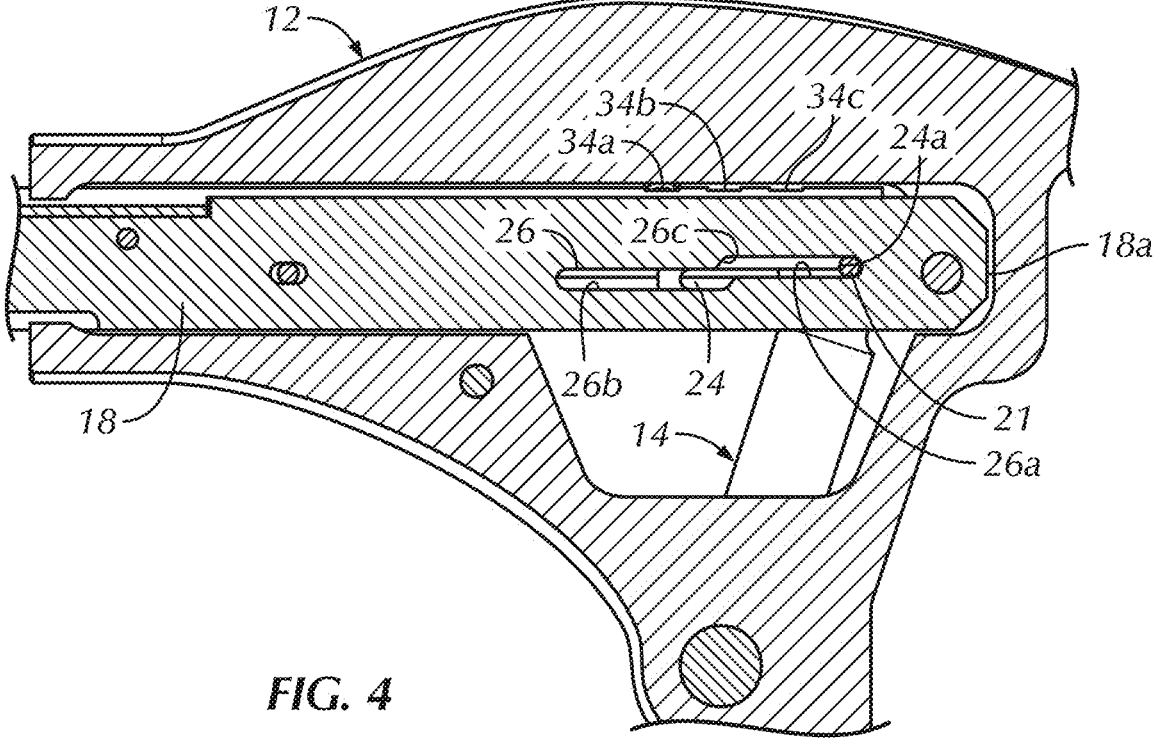
FIG. 4 is an enlarged, partial cross-sectional view of the handle and single trigger of the applicator of FIG. 1, along sectional line 4-4 of FIG. 1.

As shown in FIG. 1, the applicator 10 comprises a proximal handle 12, a single trigger 14 pivotally attached to the handle 12 (as will be further described) and a barrel 16 extending distally forward from the handle 12 to a distal end of the applicator 10. As will be described in further detail below, components of the barrel 16 include an underlying shaft 18 and a slidable, overlying elongate actuator 20. As also will be described further below, an elongate and slidable ejector rod 22 (FIGS. 2, 6C, 7C, 8C, 9B) extends through the barrel 16. Proximal ends 18a, 20a, and 22a of the respective shaft 18, elongate actuator 20 and ejector rod 22 extend into a body 12a of the handle 12. The proximal end 18a of the underlying shaft 18, as shown in FIGS. 2-4 is fixedly secured to the body 12a of the proximal handle 12. In the illustrated embodiment, the underlying shaft 18 is pinned to the body 12a, but the disclosure is not so limited and the underlying shaft 18 may be fixedly secured to the body 12a in a stationary manner via any mechanical or other methods currently known or that later become known. Conversely, the elongate actuator 20 and the ejector rod 22 are slidably received within the body 12a of the handle 12.

Turning to the proximal side of the applicator 10, the trigger 14 is pivotably attached to the handle 12 about a fulcrum 13 positioned within the body 12a of the handle 12 (underneath the barrel 16). Underlying the fulcrum 13, the trigger 14 defines a gripping portion 14a. A terminal upper end of the trigger 14 (on an opposite side of the fulcrum 13 from the gripping portion 14a) takes the form of a fork 14b (see FIG. 2) and is pivotably attached to the proximal end 22a of the ejector rod 22. As shown in FIG. 2, the proximal end 22a of the ejector rod 22 takes the form of a clevis 23, the fork 14b of the trigger 14 being inserted within, and linked to, the clevis 23 via a dowel/pin 21 extending transversely through the clevis 23 and the fork 14b.

The pin 21 extends transversely beyond the clevis 23 and through an elongate actuator slot 24 (FIG. 3) of the elongate actuator 20, positioned proximate the proximal end 20a thereof. In the illustrated embodiment, the elongate actuator 20 includes two actuator slots 24, each formed in one of the two opposing sidewalls thereof, and the pin 21 extends transversely beyond the clevis 23 in both opposing directions, but the disclosure is not so limited. Each actuator slot 24 is axially oriented, i.e., in a direction of extent of the barrel 16, and is generally linear along a majority of the axial extent thereof. A proximal end of the actuator slot 24 includes a hump or protuberance 24a extending upwardly therefrom, i.e., in a direction away from the single trigger 14. The hump 24a is generally arcuate, having an axial extent/diameter substantially equivalent to that of the pin 21 for seating the pin 21, as shown in FIG. 3. The pin 21 is transiently positioned, i.e., extends through the actuator slot 24, at the hump 24a, as will be described in further detail below.

The pin 21 extends transversely through the actuator slots 24 and extends further transversely through an elongate shaft slot 26 (FIG. 4) of the shaft 18, positioned proximate the proximal end 18a thereof. In the illustrated embodiment, the shaft 18 includes two shaft slots 26, each formed in one of the two opposing sidewalls thereof. Each shaft slot 26 is positioned laterally outwardly from the adjacent actuator slot 24. Each shaft slot 26 includes a first, proximal axial portion 26a and a second, distal axial portion 26b, joined together by a third and intermediate, transition portion 26c. In the illustrated embodiment, the first axial portion 26a is elevated in relation to the second axial portion 26b. The intermediate transition portion 26c elevationally transitions from the elevated axial portion 26a to the lower axial portion 26b. As shown best in FIG. 4, the hump 24a of the actuator slot 24 is elevationally aligned with the proximal portion 26a of the shaft slot 26 and the remainder of the actuator slot 24 is elevationally aligned with, and extends generally parallel to, the distal portion 26b of the shaft slot 26. For the sake of brevity, a single side of the pin 21, a single actuator slot 24 and a single shaft slot 26 will be described with the understanding that only a single one of each may be employed to effect the requisite function(s) thereof. As should be understood, however, in the illustrated embodiment, the actuator slot 24 and the shaft slot 26 are replicated on both opposing sides of the ejector rod 22 and the pin 21 extends transversely through both sets of actuator and shaft slots 24, 26.

Figure 5:
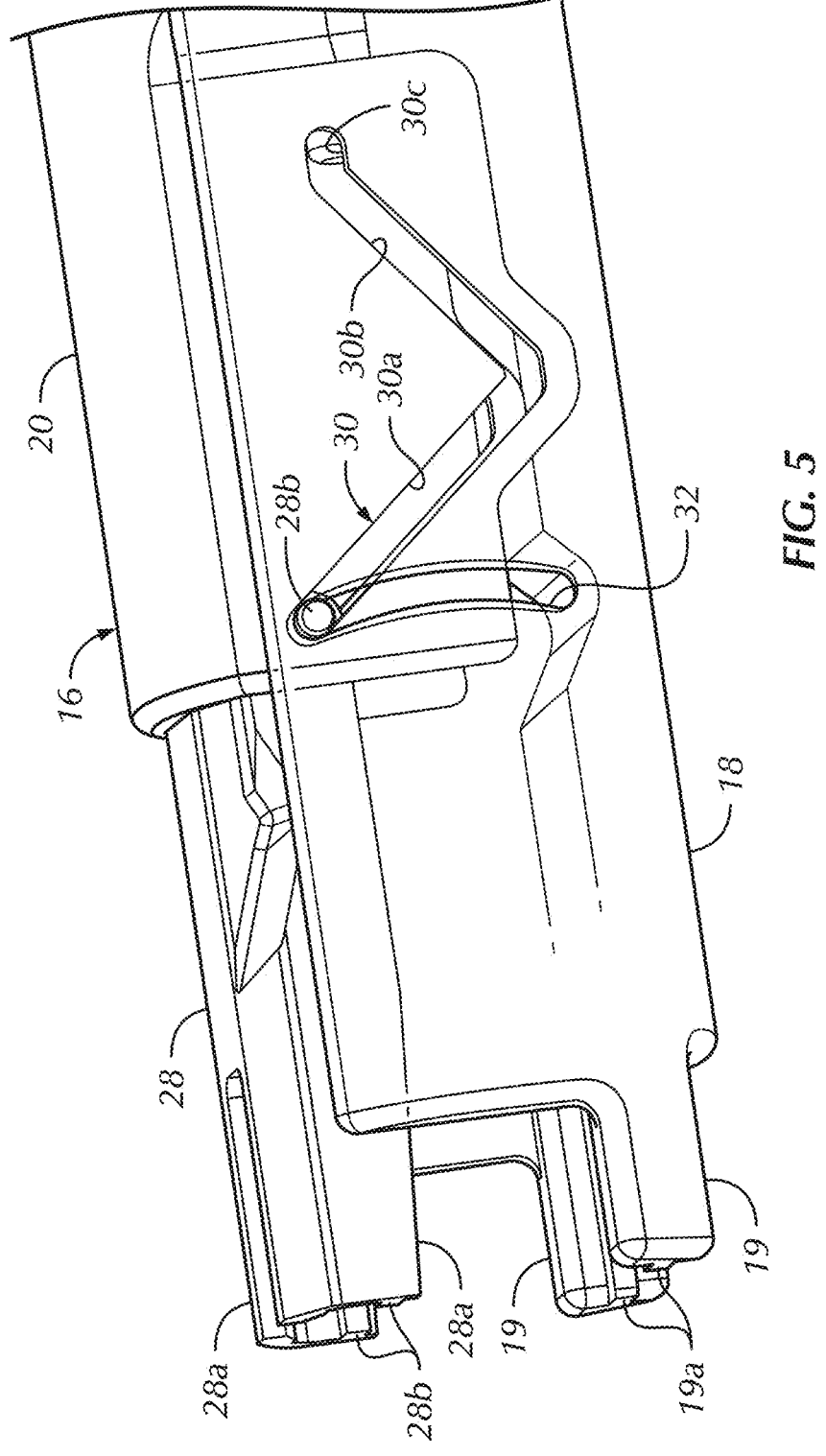
FIG. 5 is an enlarged, partial perspective view of a distal end of the applicator of FIG. 1.

Turning to the distal end of the applicator 10, as shown in FIG. 5, a jaw 28 is pivotably attached to a distal end of the elongate actuator 20. The jaw 28 is a beamed structure having a first pair of laterally spaced-apart, distally extending prongs 28a. Similarly, the elongate shaft 18 distally terminates in a second pair of laterally spaced-apart, distally extending prongs 19. The prongs 28a, 19 are configured to engage the closure device in a rotationally fixed manner. In the illustrated embodiment, each of the first and second pairs of prongs 28a, 19 include a respective pair of axially directed and laterally inwardly extending ribs 28b, 19a, respectively, configured to slidably engage the corresponding recesses 2d, 3d of the closure device 1, but the disclosure is not so limited. As should be understood, however, the first and second pairs of prongs 28a, 19 may be configured to receive other compressive closure devices.

To insert the closure device 1 into the distal end of the applicator 10, the first pair of prongs 28a are configured to releasably receive the first clamping arm 2 of the closure device 1 (via sliding of the recesses 2d onto the ribs 28b) and the second pair of prongs 19 are configured to releasably receive the second clamping arm 3 (via sliding of the recesses 3d onto the ribs 19a) of the closure device 1. The second pair of prongs 19 are fixedly secured to the elongate shaft 18 in a stationary manner. In one configuration, the second pair of prongs 19 may be monolithically formed with the elongate shaft 18, i.e., formed together as a single piece. Alternatively, the second pair of prangs 19 may be fixedly secured to the elongate shaft 18 in any stationary manner currently known or that later becomes known. Conversely, the jaw 28, including the first pair of prongs 28a, is movably coupled with the elongate actuator 20.

As shown, the jaw 28 further includes a pair of pivot dowels/pins 28b extending laterally outwardly from the jaw 28 from opposing sides thereof in opposing lateral directions. The pivot pins 28b are positioned proximate a proximal end of the jaw 28. Each pivot pin 28b extends laterally outwardly first through a respective camming slot 30 formed in a sidewall of the elongate actuator 20 proximate the distal end thereof and subsequently extends through a respective generally vertical, support slot 32 formed in a sidewall of the elongate shaft 18. As shown, the support slot 32 may be arcuate, or slightly arcuate, in the in the vertical direction.

As shown in FIGS. 5, 6C, 7C, 8C and 9C, each camming slot 30 is generally V-shaped. In a pre-use (loading) state, the respective pivot pin 28b is positioned in a distal-most position along the camming slot 30. During use, the pivot pin 28b is proximally moved along the corresponding camming slot 30. In a distal-to-proximal direction the camming slot 30 includes three continuous sections: a first leg 30a, a second leg 30b and a third leg 30c. The first leg 30a is angularly declining from an upper distal end to a lower proximal end. The second leg 30a is angularly inclined from a lower distal end to an upper proximal end. The third leg 30c is generally axially oriented.

Figures 7A, 7B, 7C:
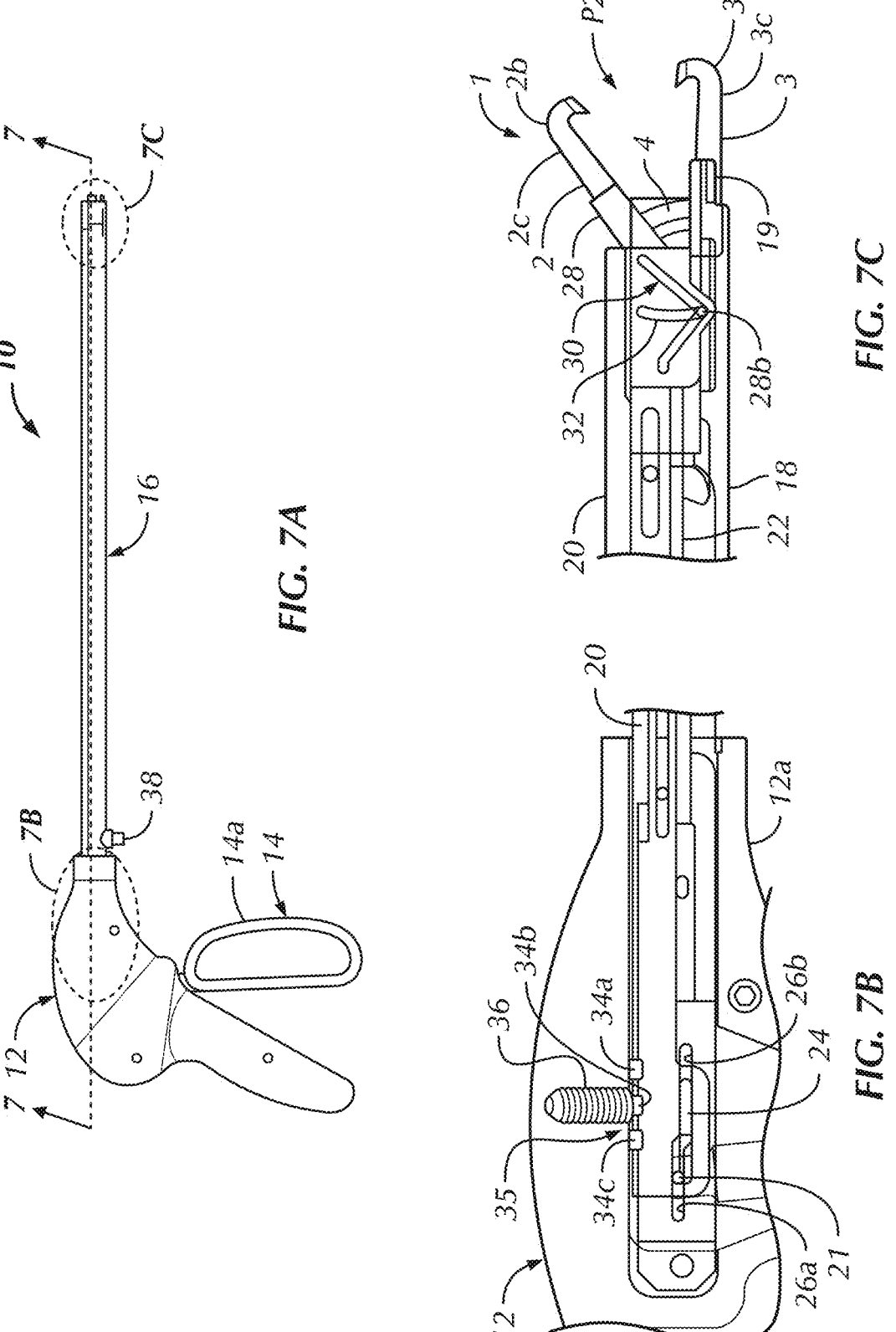
FIG. 7A is a side elevational view of the applicator of FIG. 1 in an opening position.
FIG. 7B is an enlarged, partial cross-sectional view of the handle of the applicator of FIG. 7A, taken along sectional line 7-7 of FIG. 7A.
FIG. 7C is an enlarged, partial cross-sectional view of a distal end of the applicator of FIG. 7A, taken along sectional line 7-7 of FIG. 7A.

As shown best in FIGS. 5 and 6C, the jaw 28 is initially orientated substantially parallel with the second pair of prongs 19, with the pivot pins 28b being positioned in a distal-most end of the first leg 30a of the camming slot 30 and at an uppermost end of the support slot 32. As the elongate actuator 20 advances distally relative to the stationary elongate shaft 18 (as will be described in further detail below), the coupling of the jaw 28 with the elongate shaft 18 (via the generally vertical support slot 32) results also in a sliding action between the elongate actuator 20 and the jaw 28. As the elongate actuator 20 slides distally relative to the jaw 28, the pivot pins 28*b* slide down the angularly declining first leg 30*a* of the respective camming slots 30, pivoting the jaw 28 upwards, and, thereby, opening the closure device 1 (FIG. 7C). The pivot pins 28*b* also slide down the respective support slots 32. Further distal advancement of the elongate actuator 20 relative to the jaw 28 causes the pivot pins 28*b* to slide up the angularly inclined second leg 30*b* of the respective camming slots 30 and into the axially oriented third leg 30*c* (FIGS. 8C, 9C), pivoting the jaw 28 back down into a substantially parallel orientation with the second pair of prongs 19 (FIG. 8C). The pivot pins 28*b* also slide back up the respective support slots 32.

Turning again to the proximal end of the applicator 10, a detent mechanism 35 is formed within the body 12*a* of the handle 12. As shown in FIGS. 2-4, 6B, 7B, 8B and 9B, the detent mechanism 35 includes three successive notches/depressions 34*a*, 34*b*, 34*c* formed in an upper end of the elongate actuator 20 along a portion of the actuator 20 within the body 12*a* of the handle 12. In the illustrated embodiment, the first depression 34*a* is a distal-most depression, the second depression 34*b* is a middle depression, and the third depression 34*c* is a proximal-most depression.

The detent mechanism 35 further includes a spring-loaded member 36 mounted within the body 12*a* of the handle 12 in an axially stationary manner and positioned to engage one of the three depressions 34*a*, 34*b*, 34*c*. As should be understood, the spring-loaded member 36 is configured to resist passive axial translation of the elongate actuator 20 without actively overcoming the engagement between the spring-loaded member 36 and a respective depression 34*a*, 34*b*, 34*c*. In the illustrated embodiment, the spring-loaded member 36 takes the form of a long nose spring plunger, but the disclosure is not so limited.

In use, the applicator 10 is initially provided in a loading state (FIGS. 6A-6C), wherein the spring-loaded member 36 is positioned in the first depression 34*a* (FIG. 6B). In this state, the gripping portion 14*a* of the single trigger 14 is in a furthest distal position relative to the handle 12 (FIG. 6A). As shown in FIGS. 3, 4 and 6B, in the loading state, the pin 21 is positioned within the protuberance 24*a* of the actuator slot 24 and within the proximal axial portion 26*a* of the shaft slot 26. In the loading state, and as previously described, the jaw 28 is oriented substantially parallel with the second pair of prongs 19, with the pivot pins 28*b* being positioned in a distal-most end of the first leg 30*a* of the camming slot 30 and at an uppermost end of the support slot 32. In the loading state, a closure device, such as the closure device 1, is in the first position P1 thereof and is mounted to the distal end of the applicator 10, in a manner as previously described (FIG. 6C).

Turning to FIGS. 7A-7C, the gripping portion 14*a* of the single trigger 14 is subsequently squeezed in a proximal manner (FIG. 7A) into an (closure device) opening state, wherein the spring-loaded member 36 is retracted out of the first depression 34*a* and snaped back into the second depression 34*b* (as will be described). Proximal squeezing of the single trigger 14 results in distal movement of the fork 14*b* about the intervening fulcrum 13. As the applicator 10 transitions from the loading state to the opening state, the fork 14*b*, engaging the transversely oriented pin 21, also drives the pin 21 distally.

The pin 21 distally slides along the proximal axial portion 26*a* of the shaft slot 26. The pin 21, engaged with the clevis 23, distally translates the ejector rod 22 therewith and further through the barrel 16. In the opening state, a terminal distal end 22*b* of the ejector rod 22 does not yet contact the closure device 1. The pin 21, also being positioned within the protuberance 24*a* of the actuator slot 24, is not yet slidable within the actuator slot 24 between the loading state and the opening state, but rather distally translates the elongate actuator 20 therewith and relative to the stationary elongate shaft 18 (FIG. 7B). Such distal translation of the elongate actuator 20 relative to the axially stationary spring-loaded member 36 causes the spring-loaded member 36 to retract out of the first depression 34*a* and snap back into the second depression 34*b*.

As previously described, such distal translation of the elongate actuator 20 relative to the jaw 28, as the applicator 10 transitions from the loading state to the opening state, causes the pivot pins 28*b* to slide down the angularly declining first leg 30*a* of the respective camming slots 30, pivoting the jaw 28 upwards, and, thereby, opening the closure device 1 (FIG. 7C). The closure device 1, in an open, second position P2 thereof, is placed over two lateral sides of a wound or incision, i.e., with a patient's tissue (not shown) positioned between the first and second clamping arms 2, 3.

Turning to FIGS. 8A-8C, the gripping portion 14*a* of the single trigger 14 is subsequently squeezed yet again in a proximal manner (FIG. 8A) into a (closure device) closing state, wherein the spring-loaded member 36 is retracted out of the second depression 34*b* and snaped back into the third depression 34*c* (as will be described). Proximal squeezing of the single trigger 14 results in further distal movement of the pin 21 (as previously described). As the applicator 10 transitions from the opening state to the closing state, the pin 21 distally slides further along the proximal axial portion 26*a* of the shaft slot 26 and into the intermediate, transition portion 26*c*, dropping into a proximal end of the second axial portion 26*b* of the shaft slot 26 upon reaching the closing state (FIG. 8B). The pin 21, engaged with the clevis 23, continues to further distally translate the ejector rod 22 therewith and further through the barrel 16. In the closing state, the terminal distal end 22*b* of the ejector rod 22 remains out of contact with the closure device 1.

As the applicator 10 transitions from the opening state to the closing state, the pin 21 remains positioned within the protuberance 24*a* of the actuator slot 24 and further distally translates the elongate actuator 20 therewith and relative to the stationary elongate shaft 18 (FIG. 8B). Such distal translation of the elongate actuator 20 relative to the axially stationary spring-loaded member 36 causes the spring-loaded member 36 to retract out of the second depression 34*b* and snap back into the third depression 34*c*. Upon reaching the closing state, where the pin 21 falls into the second axial portion 26*b* of the shaft slot 26, the pin 21 also drops out of the protuberance 24*a* of the actuator slot 24, enabling subsequent sliding along the axially oriented portion thereof.

As previously described, such distal translation of the elongate actuator 20 relative to the jaw 28, as the applicator 10 transitions from the opening state to the closing state, causes the pivot pins 28*b* to slide up the angularly inclined second leg 30*b* of the respective camming slots 30 and into the axially oriented third leg 30*c*, pivoting the jaw 28 back down into a substantially parallel orientation with the second pair of prongs 19 (FIG. 8C). The first clamping arm 2, therefore, clamps down onto the second clamping arm 3, with the patient's tissue (not shown) positioned therebetween, thereby fixing/clipping the clamped portion of the patient's tissue in place.

Turning to FIGS. 9A-9C, the gripping portion 14a of the single trigger 14 is subsequently squeezed one final time in a proximal manner (FIG. 9A) into an (closure device) ejecting state. Proximal squeezing of the single trigger 14 results in further distal movement of the pin 21 (as previously described). As the applicator 10 transitions from the closing state to the ejecting state, the pin 21 distally slides along the distal axial portion 26b of the shaft slot 26 (FIG. 9B). The pin 21, now positioned within the axially oriented portion of the actuator slot 24, also distally slides along the actuator slot 24. Thus, as the applicator 10 transitions from the closing state to the ejecting state, both the elongate shaft 18 and the elongate actuator 20 remain stationary. Conversely, the pin 21, engaged with the clevis 23, continues to further distally translate the ejector rod 22 therewith and further through the barrel 16. As the applicator 10 transitions from the closing state to the ejecting state, the terminal distal end 22b of the ejector rod 22 contacts and ejects/disconnects the closure device 1 from the applicator 10 (FIG. 9C).

Advantageously, with progressive proximal gripping of the trigger 14, the single trigger 14 is able to transition the applicator 10 from the loading state to the ejecting state. Further advantageously, retracting the gripping portion 14a of the trigger 14 will reverse all of the aforementioned steps to return the applicator 10 into the loading state, ready for receiving a subsequent closure device 1. As shown best in FIGS. 1, 2, 6A, 7A, 8A and 9A, the applicator 10 further includes a flush port 38 in fluid communication with the barrel 16. Between uses, the flush port 38 may be connected with a syringe (not shown) or other reservoir to flush a cleaning agent through the barrel 16 and out the distal end thereof.

It will be appreciated by those skilled in the art that changes could be made to the embodiment(s) described above without departing from the broad inventive concept thereof. It is understood, therefore, that this disclosure is not limited to the particular embodiments disclosed, but it is intended to cover modifications within the spirit and scope of the present disclosure as defined by the present description, as set forth in the appended claims.

We claim:

1. An applicator for a wound closure device, the applicator comprising:
   a proximal handle;
   a barrel extending distally from the handle, the barrel including:
      an elongate shaft secured to the handle in a stationary manner,
      a slidable, elongate actuator slidably engaged with the handle, and
      a slidable, elongate ejector rod slidably engaged with the handle;
   a jaw pivotably attached to a distal end of the elongate actuator, the jaw having a first pair of prongs, and the shaft distally terminating in a second pair of prongs, the first and second pairs of prongs being configured to releasably receive the wound closure device; and
   a single trigger attached to the handle, the single trigger being successively actuatable to multiple discrete positions:
      a first position configured to enable loading of the wound closure device to the first and second pairs of prongs, a second position wherein the loaded wound closure device is opened, and
   at least one subsequent position closing the loaded wound closure device and releasing the wound closure device from the applicator.

2. The applicator of claim 1, wherein the elongate actuator includes an actuator slot and the shaft includes a shaft slot.

3. The applicator of claim 2, wherein an upper end of the trigger defines a fork and a proximal end of the ejector rod defines a clevis, the fork being pivotably attached to the clevis via a pin, the pin also extending transversely through the actuator slot and through the shaft slot.

4. The applicator of claim 2, wherein the shaft slot includes a first, proximal axial portion and a second, distal axial portion, joined together by a third and intermediate, transition portion, the first axial portion being spaced in relation to the second axial portion.

5. The applicator of claim 1, wherein the at least one subsequent position comprises a third position closing the loaded wound closure device and a fourth position releasing the wound closure device from the applicator, and wherein successive proximal gripping of the single trigger transitions the single trigger from the first position to the fourth position, and retraction of the single trigger transitions the single trigger from the fourth position to the first position.

6. The applicator of claim 1, wherein each of the first and second pairs of prongs include a respective pair of axially directed and laterally inwardly extending ribs.

7. The applicator of claim 1, wherein the second pair of prongs are fixedly secured to the shaft in a stationary manner.

8. An applicator for a wound closure device, the applicator comprising:
   a proximal handle;
   a barrel extending distally from the handle, the barrel including:
      an elongate shaft having a shaft slot, the shaft slot including a first, proximal axial portion and a second, distal axial portion, joined together by a third and intermediate, transition portion, the first axial portion being spaced in relation to the second axial portion,
      a slidable, elongate actuator having an axially oriented and generally linear actuator slot, a proximal end of the actuator slot including a protuberance extending upwardly therefrom, wherein the protuberance is aligned with the proximal portion of the shaft slot and a remainder of the actuator slot is aligned with the distal portion of shaft slot, and
      a slidable, elongate ejector rod;
   a jaw pivotably attached to a distal end of the elongate actuator, the jaw having a first pair of prongs, and the shaft distally terminating in a second pair of prongs, the first and second pairs of prongs being configured to releasably receive the wound closure device; and
   a single trigger attached to the handle, the single trigger being successively actuatable to four discrete positions:
      a first position configured to enable loading of the wound closure device to the first and second pairs of prongs,
      a second position configured to open the loaded wound closure device,
      a third position configured to close the loaded wound closure device, and
   a fourth position configured to release the wound closure device from the applicator.

9. The applicator of claim 8, further comprising a detent mechanism, the detent mechanism comprising three successive depressions formed in an upper end of the elongate actuator and a spring-loaded member positioned to engage one of the three depressions.

10. The applicator of claim 9, wherein, in the first position of the single trigger:

(i) the spring-loaded member is positioned in a first depression of the three depressions; and (ii) the pin is positioned within the protuberance of the actuator slot and within the proximal axial portion of the shaft slot.

11. The applicator of claim 9, wherein, in the second position of the single trigger:

(i) the spring-loaded member is positioned in a second depression of the three depressions;

(ii) the pin is distally advanced within the proximal axial portion of the shaft slot relative to the position thereof in the first position of the single trigger;

(iii) the pin remains within the protuberance of the actuator slot, thereby distally advancing the elongate actuator relative to the position thereof in the first position of the single trigger; and (iv) the ejector rod is distally advanced relative to the position thereof in the first position of the single trigger.

12. The applicator of claim 9, wherein, in the third position of the single trigger:

(i) the spring-loaded member is positioned in a third depression of the three depressions;

(ii) the pin is distally advanced into the intermediate, transition portion of the shaft slot, coinciding with a proximal end of the distal axial portion of the shaft slot;

(iii) the pin exits the protuberance of the actuator slot; and (iv) the ejector rod is distally advanced relative to the position thereof in the second position of the single trigger.

13. The applicator of claim 9, wherein, in the fourth position of the single trigger:

(i) the spring-loaded member is positioned in a third depression of the three depressions;

(ii) the pin is distally advanced within the distal axial portion of the shaft slot relative to the position thereof in the third position of the single trigger;

(iii) the shaft and the elongate actuator remain in the same respective positions thereof as in the third position of the single trigger; and (iv) the ejector rod is distally advanced relative to the position thereof in the third position of the single trigger and configured to contact and eject the wound closure device from the applicator.

14. An applicator for a wound closure device, the applicator comprising:

a proximal handle;

a barrel extending distally from the handle, the barrel including:

an elongate shaft, a slidable, elongate actuator, and a slidable, elongate ejector rod;

a jaw pivotably attached to a distal end of the elongate actuator, the jaw having a first pair of prongs, and the shaft distally terminating in a second pair of prongs, the first and second pairs of prongs being configured to releasably receive the wound closure device, and wherein the jaw further includes a pin projecting laterally outwardly from the jaw and extending through a camming slot formed in a sidewall of the elongate actuator and extending through a generally vertical, support slot formed in a sidewall of the shaft; and a single trigger attached to the handle, the single trigger being successively actuatable to four discrete positions:

a first position configured to enable loading of the wound closure device to the first and second pairs of prongs, a second position configured to open the loaded wound closure device, a third position configured to close the loaded wound closure device, and a fourth position configured to release the wound closure device from the applicator.

15. The applicator of claim 14, wherein each generally vertical, support slot is generally arcuate.

16. The applicator of claim 14, wherein the camming slot defines three continuous legs, a first leg of the three continuous legs angularly declining from an upper distal end thereof to a lower proximal end thereof, a second leg of the three continuous legs angularly inclining from a lower distal end thereof to an upper proximal end thereof, and the third leg of the three continuous legs extending generally axially and proximally from the upper proximal end of the second leg.

17. The applicator of claim 16, wherein the pin is positioned proximate the upper distal end of the first leg of the camming slot and proximate an upper end of the support slot, and the first pair of prongs is oriented substantially parallel with the second pair of prongs, in the first position of the single trigger.

18. The applicator of claim 16, wherein the pin is positioned proximate the lower proximal end of the first leg of the camming slot and proximate a lower end of the support slot, and the first pair of prongs are angled away from the second pair of prongs, in the second position of the single trigger.

19. The applicator of claim 16, wherein the pin is positioned in the third leg of the camming slot, and the first pair of prongs is oriented substantially parallel with the second pair of prongs, in the third position of the single trigger.

* * * * *